United States Patent [19]

Ullman

[11] 4,160,645

[45] Jul. 10, 1979

[54] CATALYST MEDIATED COMPETITIVE PROTEIN BINDING ASSAY

[75] Inventor: Edwin F. Ullman, Atherton, Calif.

[73] Assignee: Syva Company, Palo Alto, Calif.

[21] Appl. No.: 815,636

[22] Filed: Jul. 14, 1977

[51] Int. Cl.$^2$ .................... G01N 33/16; G01N 31/10; G01N 21/22

[52] U.S. Cl. .................. 23/230 B; 23/230 R; 424/12

[58] Field of Search .................. 424/8, 12; 23/230 B, 23/230 R; 195/103.5 A; 252/408

[56] References Cited

U.S. PATENT DOCUMENTS

| | | | |
|---|---|---|---|
| 3,899,298 | 8/1975 | Szezesniak | 23/230 B |
| 3,935,074 | 1/1976 | Rubenstein | 424/12 |
| 3,966,556 | 6/1976 | Rubenstein | 424/12 |
| 3,996,345 | 12/1976 | Ullman | 424/12 |

*Primary Examiner*—Sidney Marantz
*Attorney, Agent, or Firm*—Townsend and Townsend

[57] ABSTRACT

Method and compositions are provided for competitive protein binding assays wherein a non-enzymic catalytically mediated reaction is sterically inhibited by receptors binding to a ligand to which the reaction intermediary is bound. The method employs first and second reactants, which only react with each other either very slowly or not at all. The reaction intermediary or non-enzymic catalyst provides for a two step reaction having as its final result the transformation of the first and second reactants. By conjugating the reaction intermediary to a ligand, whereby the presence of receptor bound to the ligand inhibits the approach of one or both of the reactants, ligand and antiligand can be determined. Alternatively, anticatalyst can be employed which is inhibited from binding to the catalyst when antiligand is bound to ligand. The binding of anticatalyst to catalyst inhibits the catalytically mediated reaction. By comparing the rate of reaction with an unknown amount of analyte present to rates with known amounts of analyte, the concentration of the analyte in an unknown may be determined.

27 Claims, No Drawings

CATALYST MEDIATED COMPETITIVE PROTEIN BINDING ASSAY

BACKGROUND OF THE INVENTION

1. Field of the Invention

A wide variety of techniques exist for the determination of specific organic compounds which are present at extremely low concentrations, generally 1 μg/ml or less. One group of techniques referred to as competitive protein binding assays involve the employment of a receptor which is capable of recognizing a specific polar and spatial organization, referred to as an epitopic site.

Members of these types of assays, such as radioimmunoassay (RIA) and heterogeneous enzyme immunoassay (ELISA) involve labeling a ligand, allowing for a competition between the labeled ligand and ligand in the sample for a limited amount of receptor, and separating labeled ligand bound to receptor and unbound labeled ligand. Newer techniques avoid the separation step, either relying on a free radical label (FRAT ®) or employing a homogeneous enzyme immunoassay (EMIT ®), where the label is conjugated to the ligand and the presence of receptor bound to the ligand either changes the spectral properties of the free radical or the enzymatic activity of the enzyme.

Despite the number of different competitive protein binding assays which are presently available, there is still a desire to provide new techniques with enhanced sensitivity, simpler protocols, stabler reagents, easier modes of preparation of reagents, and the like. Other considerations include reduced sensitivity to interferants which may be present in samples, ease of measurement and the like.

2. Brief Description of the Prior Art

U.S. Pat. No. 3,690,834 describes a free radical competitive protein binding assay. U.S. Pat. No. 3,817,837 describes a homogeneous enzyme immunoassay. U.S. Pat. Nos. 3,998,943 and 3,996,345 describe fluorescent competitive protein binding assays.

SUMMARY OF THE INVENTION

Competitive protein binding assays and reagents are provided involving three interrelated reactants capable of undergoing electron transfer reactions. One of the reactants (A) reacts by receiving or transferring two electrons, for example, hydride transfer. Another of the reactants (B) reacts by receiving or transferring a single electron, and reacts slowly, if at all, with A. The third reactant (C), referred to as catalyst, is capable of receiving and transferring both 1 and 2 electrons and reacts rapidly with both A and B.

By conjugating C to a ligand, the binding of antiligand to the conjugate inhibits the approach of either or both A and B to C, so that the amount of available antiligand modulates the transformation of A and B to products.

Alternatively, anticatalyst can be included in the assay medium which is inhibited from binding to the catalyst when antiligand is bound to the ligand. When anticatalyst is bound to catalyst, A and B are inhibited from approaching C.

Since available antiligand for binding to the conjugate will be related to the amount of antiligand in an unknown or the amount of ligand in an unknown in combination with a predetermined amount of antiligand, the rate of transformation of A and B will be related to the amount of antiligand or ligand in an unknown.

Reagent kits can be provided whereby the amount of the conjugate, and reactants A and B are present in predetermined ratios, along with antiligand for assays for ligand, and optionally anticatalyst, so as to substantially optimize the sensitivity of the assay.

DESCRIPTION OF THE SPECIFIC EMBODIMENTS

A novel competitive protein binding assay is provided employing a non-enzymic intermediate compound which is capable of greatly accelerating the rate of reaction between two other compounds, which react, if at all, with each other at an extremely slow rate. The method is predicated upon employing electron transfer reactants, whereby mechanistically one compound reacts with the transfer of two electrons and the other compound reacts with the transfer of one electron. The intermediate is capable of reacting with both. The intermediate compound is conjugated to a ligand and the approach of one or both of the reactants to the intermediate compound is affected by the adjacent presence of ligand receptor. The rate of the reaction between the two reactants is related to the amount of ligand receptor available for binding to the intermediate-ligand conjugate.

In an assay for ligand, by employing a predetermined amount of ligand receptor, the amount of ligand receptor available for binding to the conjugate will vary with the amount of ligand in the unknown. In an assay for ligand receptor, the amount available will be directly related to the amount of ligand receptor present in the unknown. By relating rates determined with an unknown with rates determined with known amounts of ligand or ligand receptor, the amount of ligand or ligand receptor present in an unknown can be determined.

The reagents can be conveniently provided in kit form where the amounts provided are chosen so as to substantially optimize the sensitivity of the assay.

Definitions

Analyte — the compound or composition to be measured, which may be a ligand which is mono- or polyepitopic, antigenic or haptenic, a single or plurality of compounds which share at least one common epitopic site or a receptor.

Ligand — any compound for which a receptor naturally exists or can be prepared.

Ligand Analog — a modified ligand which can compete with the analogous ligand for receptor, the modification providing means to join a plurality of ligand analogs in a single molecule or to provide a means for directing lables to sites on a ligand.

Poly(ligand analog) — a plurality of ligand analogs joined together covalently, normally to a hub nucleus, to provide a compound having a plurality of epitopic sites capable of competing with the analogous ligand for receptor.

Label — a compound capable of being either oxidized or reduced by either one or two electron transfer. The label is also referred to as catalyst and serves to catalyze the reaction between the redox reactants. The label is non-enzymic and generally below 2,000 molecular weight.

Receptor — any compound or composition capable of recognizing a particular spatial and polar organization of a molecule i.e. epitopic site. Illustrative receptors include naturally occurring receptors, antibodies, enzymes, Fab fragments and the like. For any specific ligand, the receptor will be referred to as anti(ligand). The receptor — antiligand — and its reciprocal ligand from an immunological pair.

Redox reactants — the redox reactants are compounds capable of undergoing reduction or oxidation, which react with each other, if at all, at a slow rate. The redox reactants include, one reactant — $R^1$ — which undergoes reduction-oxidation by a one electron transfer with the label reactant, another — $R^2$ — which undergoes reduction-oxidation by a two electron transfer with the label. Illustrative of two electron transfers are the transfers of hydride ions or the oxidation-reduction of metals which involves two electrons e.g. $SN^{++}$ to $Sn^{+4}$ and $Tl^+$ to $Tl^{+3}$. Illustrative one electron transfers include reaction of viologens, metal redox reactions e.g. $Fe^{+3}$ to $Fe^{+2}$, and $Cu^{++}$ to $Cu^+$ and stable free radicals to anions.

Labeled Ligand — ligand having at least one label covalently bonded to it and retaining at least one epitopic site.

Poly(ligand analog)-polylabel — a composition whereby a plurality of ligand analogs and a plurality of labels are bonded to a water soluble polyfunctionalized hub nucleus, whereby the ligand analog and label are in juxtaposition, so that when receptor is bound to ligand analog, the approach to the label of antilabel or at least one of the electron transfer reactants is inhibited.

Assay

The subject assay is carried out in an aqueous, normally homogeneous, zone at a moderate pH, generally close to optimum assay sensitivity. The assay zone for the determination of analyte is prepared by employing an appropriately buffer aqueous solution, the unknown sample, which may have been subject to prior treatment, labeled ligand, electron transfer reactants $R^1$ and $R^2$, and as appropriate poly(ligand analog)-polylabel and antilabel.

The presence of antiligand or ligand in combination with a predetermined amount of antiligand in the assay medium controls the degree to which antiligand is bound to labeled ligand to inhibit the approach of either or both of the redox reactants to the label or the finding of antilabel to the label, which inhibits the approach of both of the reactants to the label. Therefore, the antiligand present in the assay medium when bound to ligand sterically acts to affect the rate at which the redox reactants, $R^1$ and $R^2$, react with the label.

The assay is predicated on the fact that the slower of the rates of $R^1$ with label and $R^2$ with label is substantially greater than the rate of reaction of $R^1$ with $R^2$ at the concentration employed in the medium. The rate of the label mediated reaction between $R^1$ and $R^2$ as compared to the rate of the direct reaction between $R^1$ and $R^2$ should be at least $10^2$ greater, usually at least $10^4$ greater and preferably at least $10^6$ greater. The significant factor is the amount of background signal generated by the direct reaction between $R^1$ and $R^2$ as compared to the signal generated by the label mediated reaction.

In carrying out the assay an aqueous medium will normally be employed. Other polar solvents may also be employed, usually oxygenated organic solvents of from one to six, more usually from one to four carbon atoms, including alcohols, ethers and the like. Usually, these cosolvents will be present in less than about 40 weight percent, more usually in less than about 20 weight percent.

The pH for the medium will usually be in the range from about 5 to 10, more usually in the range from about 7 to 9. Various buffers may be used to achieve the desired pH and maintain the pH during the determination. Illustrative buffers include borate, phosphate, carbonate, Tris, barbital and the like. The particular buffer employed is not critical to this invention, but in individual assays, one buffer may be preferred over another.

Moderate temperatures are normally employed for carrying out the assay and usually constant temperatures during the period of the assay will be employed. The temperatures will normally range from about 10° to 50° C., more usually from about 15° to 40° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique and the concentration of the analyte of interest will normally determine the concentration of the other reagents.

While the concentrations of the various reagents will generally be determined by the concentration range of interest of the analyte, the final concentrations will normally be determined empirically to optimize the sensitivity of the assay over the range of interest. Since the binding constant and binding profile of receptors will vary, for example, with antibodies from bleed to bleed, each new batch of antibodies may require different concentration ratios for the different reagents.

Normally, for mono- and polyepitopic ligand analytes the concentration of antiligand based on binding sites will be about 1 to 50 times either the minimum or maximum concentration of interest based on epitopic sites, usually about 1 to 10 times and more usually 1 to 3 times the maximum concentration of interest. For polyepitopic ligand receptor analytes, the equivalent ratio of receptor analyte to labeled ligand will generally be in the range of about 0.01-100 as to a concentration of receptor analyte to in the range of interest. For polyepitopic ligand analytes the concentration of labeled ligand will be about equal to the minimum concentration of interest normally not exceeding the maximum concentration of interest, generally not less than $10^{-4}$ more usually not less than $10^{-2}$ of the minimum concentration of interest. For monoepitopic ligand analytes and monoepitopic ligand receptor analytes, based on binding sites, the concentration of poly(ligand analog)-polylabel will be about equal to the minimum concentration of interest, normally not exceeding the maximum concentration of interest, generally not less than $10^{-4}$, more usually not less than $10^{-2}$ of the minimum concentration of interest. Concentration ranges of interest will generally be in the range from about $10^{-3}$ to $10^{-14}$g/ml.

The concentration of electron transfer reactants may be varied widely, subject to certain considerations. The first consideration is that the concentration will generally not be rate limiting. Desirably, the observed rate will be independent of the changes in concentration of the redox reactants during the period of measurement. A second consideration is the difference in the catalyzed and uncatalyzed rates. Where there is a significant uncatalyzed rate, it will generally be desirable to enhance the concentration of only one of the electron transfer agents, while maintaining the other electron transfer agent at a relatively low concentration. This will be particularly true where the rate of reaction between the catalyst and one of the electron transfer reagents is very fast as compared to the reaction of the catalyst and the other of the electron transfer reagents. Conveniently, the concentration of the electron transfer reagents will generally be in the range of about $10^{-2}$ to $10^{-9}$M, more usually in the range of about $10^{-3}$ to $10^{-6}$M.

The amount of antilabel employed based on binding sites will normally be in the range of about 0.1 to 100 times the number of label molecules in the assay medium, more usually in the range of about 1 to 10.

The order of addition of the various reagents may vary widely, depending upon how the reaction is initiated, the nature of the analyte, and the relative concentrations of ligand, receptor and labeled ligand. Conveniently, in an assay for ligand, the unknown sample suspected of containing the ligand or antiligand may be first combined, the mixture incubated, followed by addition of the labeled ligand and a second incubation or alternatively, the unknown sample, labeled ligand and antiligand combined simultaneously and incubated. Usually, one of the electron transfer agents may be added at any time, but the other electron transfer agent will usually be added in a final step to initiate the reaction.

Where antilabel is employed, it will usually be added concomitantly with or preferably after combining labeled ligand (includes poly(ligand analog)-polylabel) and antiligand and before the redox reactants are added.

As indicated above, either a competitive or equilibrium mode may be employed, where the ligand and labeled ligand compete for antiligand or the ligand is first combined with antiligand, so that any remaining antiligand may then combine with labeled ligand.

Depending upon the mode employed, equilibrium or nonequilibrium, the rate of binding of the antiligand to ligand and labeled ligand, and the relative concentrations of the ligand, labeled ligand and antiligand, one or more incubation steps may be involved. Normally, times between additions may vary from a few seconds to many hours, usually not exceeding 16 hrs., more usually not exceeding 6 hrs. Usually incubation times will vary from about 0.5 min. to 1 hr., more usually from about 0.5 min. to 30 min. Since the ultimate result will be dependent upon the results obtained with standard(s) treated in substantially the same manner, and when possible in the identical manner, the particular mode and periods of time are not critical, so long as significant reproducible differentiations are obtained with varying concentrations of analyte.

Depending upon the choice of assay protocol, the equipment employed and the concentration of analyte involved, assay volumes may be as small as about 1 $\mu$l, more usually being about 25 $\mu$l, and will usually not exceed 5 ml, more usually not exceeding 2 ml.

The assay measurement will normally depend upon measuring electromagnetic radiation at a particular wavelength or a narrow band of wavelengths in various ranges, such as radio frequency, ultraviolet, visible, etc., although other measurements may be made e.g. electrical. For electromagnetic measurements, the absorption or emission of radiation will be involved.

Depending upon the nature of the electron transfer reagents, various techniques may be employed. For the most part the techniques employed will involve the absorption or emission of electromagnetic radiation. Such techniques may involve fluorescence, chemiluminescence, ultraviolet or visible light absorption, electron spin resonance, and the like.

While it will be generally desirable to directly follow the formation of one of the products of the electron transfer reagents, in some instances the product may be coupled with another reaction to obtain the desired signal. For example, where hydrogen peroxide is a redox reactant product, it may be more efficient to introduce a chemiluminescer under conditions where the chemiluminescer reacts with the hydrogen peroxide to provide chemiluminescence. In other instances, where a change in a metal oxidation state is involved, it may be desirable to introduce a complexing agent which reacts with the metal ion product to produce a dye. The concentration of such additives will be proportional to the efficiency of the reaction of the electron transfer reagent product and the ancillary reagent, the sensitivity with which the resulting product may be measured and the rate at which the electron transfer reagent product and the ancillary reagent react.

In the assay for antiligand, the primary difference will be that no antiligand need be added and the unknown will be combined with labeled ligand and incubated or the electron transfer reagents added concomitantly with the unknown and labeled ligand.

Materials

The primary components in the subject assay for analyte are: the analyte; labeled ligand (includes poly(ligand analog)-polylabel); electron transfer reagents; optionally antilabel; and in assays for ligand as analyte, antiligand.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations or assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:

protamines
histones
albumins
globulins
scleroproteins
phosphoproteins
mucoproteins chromoproteins
lipoproteins
nucleoproteins
glycoproteins
unclassified proteins, e.g. somatotropin, prolactin, insulin, pepsin A number of proteins found in the human plasma are important clinically and include:

Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
$\alpha_1$-glycoprotein
$\alpha_1\chi$-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
  (IgG) or $\gamma$G-globulin
Mol. formula:
  $\gamma_2\kappa_2$ or $\gamma_2\lambda_2$
Immunoglobulin A (IgA)
  or $\gamma$A-globulin
Mol. formula:
  $(\alpha_2\kappa_2)^n$ or $(\alpha_2\lambda_2)^n$
Immunoglobulin M
  (IgM) or $\gamma$M-globulin
Mol. formula:
  $(\mu_2\kappa_2)^5$ or $(\mu_2\lambda_2)^5$
Immunoglobulin D(IgD)
  or $\gamma$D-Globulin ($\gamma$D)
Mol. formula:
  $(\delta_2\kappa_2)$ or $(\delta_2\lambda_2)$
Immunoglobulin E (IgE)
  or $\gamma$E-Globulin ($\gamma$E)
Mol. formula:
  $(\epsilon_2\kappa_2)$ or $(\epsilon_2\lambda_2)$
Free K and $\gamma$ light chains
Complement factors:
C'1
  C'1q
  C'1r
  C'1s
C'2
C'3
  $\beta_1$A
  $\alpha_2$D
C'4
C'5
C'6
C'7
C'8
C'9

Important blood clotting factors include:

| BLOOD CLOTTING FACTORS | |
|---|---|
| International designation | Name |
| I | Fibrinogen |
| II | Prothrombia |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromoboplastin component (PTC) |
| X | Stuart-Prower factor, autoprothrombin III |
| XI | Plasma thromboplastin antecedant (PTA) |
| XII | Hagemann factor |
| XIII | Fibrin-stabilizing factor |

Important protein hormones include:

Peptide and Protein Hormones

Parathyroid hormone
  (parathormone)
Thyrocalcitonin
Insulin
Glucagon
Relaxin
Erythropoietin
Melanotropin
  (melanocyte-stimulating hormone; intermedin)
Somatotropin
  (growth hormone)
Corticotropin
  (adrenocorticotropic hormone)
Thyrotropin
Follicle-stimulating hormone
Luteinizing hormone
  (interstitial cell-stimulating hormone)
Luteomammotropic hormone
  (luteotropin, prolactin)
Gonadotropin
  (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)

CRF, LRF, TRF, Somatotropin-RF, GRF, FSH-RF, PIF, MIF

Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrhoeae | Polysaccharide |
| Corynebacterium diphtheriae | Polysaccharide |
| Actinobacillus mallei; | Crude extract |
| Actinobacillus whitemori | |
| Francisella tularensis | Lipopolysaccharide |
| | Polysaccharide |
| Pasteurella pestis | |
| Pasteurella pestis | Polysaccharide |
| Pasteurella multocida | Capsular antigen |
| Brucella abortus | Crude extract |
| Heamophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide |
| | Polysaccharide |
| Salmonella typhi-murium; | Polysaccharide |
| Salmonella derby | |
| Salmonella pullorum | |
| Shigella dysenteriae | Polysaccharide |
| Shigella flexneri | |
| Shigell sonnei | Crude, polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria

Corynebacterium diptheriae

Pneumococci

Diplococcus pneumoniae

Streptococci

Streptococcus pyogenes
Streptococcus salivarus

Staphylococci

Staphylococcus aureus
Staphylococcus albus

Neisseriae

Neisseria meningitidis
Neisseria gonorrheae

Enterobacteriaciae

Escherichia coli  ⎫
Aerobacter aerogenes  ⎬ The coliform bacteria
Klebsiella pneumoniae  ⎭

Salmonella typhosa  ⎫
Salmonella choleraesuis  ⎬ The Salmonellae
Salmonella typhimurium  ⎭

Shigella dysenteriae  ⎫
Shigella schmitzii  ⎪
Shigella arabinotarda  ⎪
Shigella flexneri  ⎬ The Shigellae
Shigella boydii  ⎪
Shigella Sonnei  ⎭

Other enteric bacilli

Proteus vulgaris  ⎫
Proteus mirabilis  ⎬ Proteus species
Proteus morgani  ⎭
Pseudomonas aeruginosa
Alcaligenes faecalis
Vibrio cholerae

Hemophilus-Bordetella group

Hemophilus influenzae,   H. ducreyi
                         H. hemophilus
                         H. aegypticus
                         H. paraiufluenzae Bordetella pertussis

Pasteurellae

Pasteurella pestis
Pasteurella tulareusis

Brucellae

Brucella melitensis
Brucella abortus
Brucella suis

Aerobic Spore-forming Bacilli

Bacillus anthracis
Bacillus subtilis
Bacillus megaterium
Bacillus cereus

Anaerobic Spore-forming Bacilli

Clostridium botulinum
Clostridium tetani
Clostridium perfringens
Clostridium novyi
Clostridium septicum
Clostridium histolyticum
Clostridium tertium
Clostridium bifermentans
Clostridium sporogenes

Mycobacteria

Mycobacterium tuberculosis hominis
Mycobacterium bovis
Mycobacterium avium
Mycobacterium leprae
Mycobacterium paratuberculosis

Actinomycetes (fungus-like bacteria)

Actinomyces israelii
Actinomyces bovis
Actinomyces naeslundii
Nocardia asteroides
Nocardia brasiliensis

| The Spirochetes | |
|---|---|
| Treponema pallidum | Spirillum minus |
| Treponema pertenue | Streptobacillus moniliformis |
| Treponema carateum | |
| Borrelia recurrentis | |
| Leptospira icterohemorrhagiae | |
| Leptospira canicola | |

Mycoplasmas

*Mycoplasma pneumoniae*

Other pathogens

*Listeria monocytogenes*
*Erysipelothrix rhusiopathiae*
*Streptobacillus moniliformis*
*Donvania granulomatis*
*Bartonella bacilliformis*

Rickettsiae (bacteria-like parasites)

*Rickettsia prowazekii*
*Rickettsia mooseri*
*Rickettsia rickettsii*
*Rickettsia conori*
*Rickettsia australis*
*Rickettsia sibiricus*
*Rickettsia akari*
*Rickettsia tsutsugamushi*
*Rickettsia burnetii*
*Rickettsia quintana*

Chlamydia (unclassifiable parasites bacterial/viral)

Chlamydia agents (naming uncertain)

Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifer (Absidia corymbifera)*
*Rhizopus oryzae*
*Rhizopus arrhizus* } Phycomycetes
*Rhizopus nigricans*
*Sporotrichum schenkii*
*Fonsecaea pedrosoi*
*Fonsecaea compacta*
*Fonsecaea dermatitidis*
*Cladosporium carrionii*
*Phialophora verrucosa*
*Aspergillus nidulans*
*Madurella mycetomi*
*Madurella grisea*
*Allescheria boydii*
*Phialosphora jeanselmei*
*Microsporum gypseum*
*Trichophyton mentagrophytes*
*Keratinomyces ajelloi*
*Microsporum canis*
*Trichophyton rubrum*
*Microsporum andouini*

Viruses

Adenoviruses

Herpes viruses

*Herpes simplex*
Varicella (Chicken pox)
Herpes Zoster (Shingles)
Virus B
Cytomegalovirus Pox Viruses Variola (smallpox)
Vaccinia
*Poxvirus bovis*
Paravaccinia
*Molluscum contagiosum*

Picornaviruses

Poliovirus
Coxsackievirus
Echoviruses
Rhinoviruses

Myxoviruses

Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus Arboviruses Eastern Equine Eucephalitis Virus
Western Equine Eucephalitis Virus
Sindbis Virus
Chikungunya Virus
Semliki Forest Virus
Mayora Virus
St. Louis Encephalitis Virus
California Encephalitis Virus
Colorado Tick Fever Virus
Yellow Fever Virus
Dengue Virus Reoviruses Reovirus Types 1-3

Hepatitis

Hepatitis A Virus
Hepatitis B Virus

Tumor Viruses

Rauscher Leukemia Virus
Gross Virus
Maloney Leukemia Virus the monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids; isoquinoline alkaloids; quinoline alkaloids; which includes quinine and quinidine; diterpene alkaloids, their derivatives and metabolites.

The next group of drugs includes steroids, which includes the estrogens, gestrogens, androgens, andrenocortical, bile acids, cardiotonic glycosides and aglycones, which includes digoxin and digoxigenin, saponins and sapogenins, their derivatives and metabolites. Also included are the steroid mimetic substances, such as diethyl stilbestrol.

The next group of drugs is cyclic lactams having from 5 to 6 membered rings, which include the barbiturates, diphenyl hydantoin, and their metabolites.

The next group of drugs is aminoalkyl benzenes, with alkyl of from 2 to 3 carbon atoms, which includes the amphetamines, catecholamines, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, C, D, E and K.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucelotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propanolol, griseofulvin, butyrophenones, antihistamines, anticholinergic drugs, such as atropine, their metabolites and derivatives.

The next group of compounds is amino acids and small peptides which include thyroxin, triiodothyronine, oxytocin, ACTH, angiotensin, gentamycin, met- and leu-enkephalin their metabolites and derivatives.

Metabolites related to diseased states include spermine, galactose, phenylpyruvic acid, and porphyrin type 1.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or higher molecular weight, including such materials as avidin, thyroxine bind globulin, thyroxine binding prealbumin, transcortin, etc.

Poly(ligand analog)-polylabel

For monoepitopic ligand analytes, the label may be conjugated to the ligand or a polyepitopic composition may be prepared having a plurality of epitopic sites capable of competing with the ligand and capable of being labeled with the label which acts as catalyst. Where the label is directly conjugated to the ligand, it may be necessary to introduce a linking group or functionality in either or both the ligand or label. Where functionalities are present in the ligand and the label which provide for the formation of a covalent bond e.g. carboxy and amino or oxo-carbonyl and amino, the two compounds may be linked directly. Alternatively, a linking group may be provided. The same types of linking groups which are employed for joining the ligand and label to a hub nucleus may be employed for joining the ligand and the label directly.

The preparation of the polyepitopic composition normally involves modification of the ligand to provide for a linking group between a ligand and a hub nucleus, which is normally a water soluble polymer and conveniently a poly(amino acid) or polysaccharide.

Usually, the hub nucleus will be from about 25,000 to 600,000 molecular weight, more usually from about 30,000 to 300,000 molecular weight. The linking group may be a bond, but will more conveniently be a divalent organic group, usually aliphatic having not more than one site of ethylenic unsaturation, having from 0 to 6, more usually from 1 to 4 and preferably from about 1 to 2 heteroatoms, which are oxygen, nitrogen and sulfur, preferably oxygen and nitrogen, wherein oxygen is bonded solely to carbon as oxy(ether) or nonoxocarbonyl and nitrogen is bonded to carbon e.g. tertiary-amino or as amido, while sulfur is analogous to oxygen.

The functionalities involved in linking normally include alkylamine, amide, amidine, thioamide, urea, thiourea and guanidine.

Illustrative functionalities involved in linking are carboxylic acids in conjunction with diimides, mixed anhydrides with carbonate monoesters, aldehydes in conjunction with reductants e.g. borohydrides, imidoesters, active carboxylic esters e.g. N-hydroxy succinimide or p-nitrophenyl, isocyanates, isothiocyanates, active halide, and the like.

Normally, the monoepitopic ligand will be modified to introduce a group which is active or activatable, followed by combining the modified ligand with the hub molecule so as to polysubstitute the hub molecule. Normally, there will be at least one ligand molecule per 50,000 molecular weight of the hub molecule, more usually at least one per 25,000 molecular weight and usually not more than one per 1,500 molecular weight. Illustrative hub molecules include albumins, globulins, cellulose, dextran, and the like. That is, those compositions which have active functionalities such as amino and hydroxyl, which can be readily substituted and remain soluble in an aqueous solution.

For an extensive discussion of linking groups for haptens to poly(amino acids) see U.S. Pat. No. 3,817,837, the appropriate portions of which are incorporated herein by reference.

The label may be linked to the hub nucleus in the same manner as described for linking the ligand analog. The ratio of number of labels per unit molecular weight of the hub nucleus will be in the same ranges as that for the ligand analog. However, it will usually be preferable to have at least about 0.5 ligand analogs per label, more usually at least one ligand analog per label and generally not more than about 5 ligand analogs per label. The significant factor is the degree of steric inhibition provided by antiligand binding to ligand analog to approach of one of the electron transfer agents or the antilabel to the label.

Electron transfer agents and label

As indicated previously, the family of electron transfer agents involves an electron transfer agent which acts by the transferring of two electrons ($R^2$), an electron transfer reagent which acts by the transferring of one electron ($R^1$) and an intermediate or catalyst agent which serves as the label and is able to receive and transfer one and two electrons. In some instances, the intermediate or catalyst may react as either $R^1$ or $R^2$, where the particular catalyst cannot react with a particular electron transfer reagent or family of reagents.

The label will for the most part be either metal complexes or aromatic compounds capable of assuming a neutral or charged quinone structure with a heteroatom of atomic number 7 to 8 i.e. oxygen and nitrogen. For the most part, the label will be aromatic having from one to five, usually one to four, fused or non-fused rings, where one or more heteroatoms may be involved as annular atoms. The labels will be able to assume either an o-quinone or p-quinone structure, either outside of or as part of a cyclic structure. Therefore, common to the label which does not involve a metal will be the following formulii.

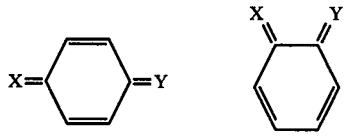

where X and Y can be the same or different and X is oxygen or nitrogen and Y is oxygen, nitrogen or carbon, and wherein X and Y, as well as the annular atoms may be further substituted.

The first group of compounds are the quinones, either ortho or para, where the heteroatoms are not involved in a heterocyclic structure. These compounds will for the most part have the following formulii.

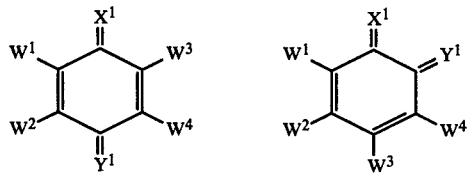

wherein $X^1$ and $Y^1$ are oxygen or imino, more usually oxygen;
$W^{1-4}$ may be hydrogen, halogen, particularly of atomic number 9 to 35, more particularly of atomic number 17 to 35, alkyl of from 1 to 6 carbon atoms, more usually of from 1 to 4 carbon atoms or W groups on adjacent carbon atoms, particularly $W^1$ and $W^2$ or $W^3$ and $W^4$ may be taken together to form an aromatic ring, particularly a benzene ring, either substituted or unsubstituted, normally having not more than about 2 substituents which are alkyl or heteroatom of atomic numbers 7 to 8, which include hydroxy, alkoxy, amino having from 0 to 2 alkyl groups, e.g. alkylamino, and dialkylamino, wherein the alkyl groups are of from 1 to 6, more usually of from 1 to 3 carbon atoms.

Generally, the quinones will have from 1 to 3 rings, usually fused rings, and will be of from about 6 to 20 carbon atoms, more usually of from about 6 to 16 carbon atoms. The total number of heteroatoms will generally be in the range of from about 2 to 8, more usually from 2 to 6.

Illustrative quinones include alizarin, 1,2-naphthoquinone, chloranil, 2,6-dichlorophenolindophenol and 2,6-dibromophenolindophenol.

In each instance, the label would be appropriately modified to include a linking group for conjugation to the ligand. Linking groups have been previously discussed in relationship to the ligand analog.

The next group of compounds are those which are basically internal o-quinonediimines. These compounds for the most part will have the following formulii.

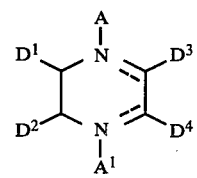

wherein:
the broken lines indicate the presence or absence of a double bond, the double bonds normally being present in the oxidized form, usually not more than one of the double bonds being present in the reduced form;
A and $A^1$ may be the same or different and may be an unshared pair of electrons, hydrogen, alkyl of from 1 to 6 carbon atoms, hydroxyalkyl of from 5 to 6 carbon atoms, particularly sugars e.g. ribityl, A and $A^1$ normally being other than hydrogen when the broken line forms a double bond, and usually one of A and $A^1$ is other than hydrogen or an unshared pair of electrons.
$D^{1-4}$ may be the same or different and are hydrogen, halo, particularly chloro, oxy e.g. alkoxy of from 1 to 6, usually 1 to 3 carbon atoms, or amino having from 0 to 2 alkyl groups of from 1 to 6, usually 1 to 3 carbon atoms, or
each of the pairs of $D^1$ and $D^2$ and $D^3$ and $D^4$ may be taken together to form six membered rings, which with the atoms to which they are attached will be substituted (see the above substituents) or unsubstituted carbocyclic or heterocyclic aromatic rings having six annular members, having from 0 to 2 nitrogen annular members and having from 0 to 4, usually 2 to 4 substituents on the rings which may be alkyl of from one to six carbon atoms, more usually of from one to four carbon atoms, oxy, which is hydroxy or alkoxy, or amino, alkylamino or dialkylamino (0 to 2 alkyl groups) wherein the alkyl groups are of from 1 to 6, more usually of from 1 to 3 carbon atoms e.g. methyl.

Instances where a cyclic lactam is involved, will be treated in this invention as their enol form.

The compounds will be of from 5 to 20 carbon atoms, more usually of from 12 to 18 carbon atoms and having 2 to 8 heteroatoms, more usually 2 to 6 heteroatoms, and preferably 4 to 6 heteroatoms which are oxygen and nitrogen.

Where positive nitrogen is involved, there will normally be an anionic counterion, which may be any anion in solution, usually being halo e.g. chloro and bromo, sulfate, phosphate or borate.

Illustrative compounds include flavins, e.g. flavin, riboflavin, galactoflavin, and lumiflavin, pyocyanine, neutral red, safranine and phenazine methosulfate.

The next group of compounds are biaryls which will have the following formula wherein:

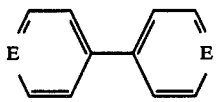

E is carbon substituted nitrogen, wherein the substituents are alkyl of from 1 to 10, usually of from 1 to 8 carbon atoms, or aminocarbon e.g. C-NJ$_2$, wherein the carbon is an annular member and the amino group has from 0 to 2 alkyl substituents (J), usually 2 alkyl substituents of from 1 to 6 carbon atoms, more usually of from 1 to 3 carbon atoms.

The compounds will normally have from 12 to 30 carbon atoms, more usually from 12 to 26 carbon atoms, generally having from 2 to 4 heteroatoms which are nitrogen and oxygen, particularly nitrogen.

Illustrative compounds include methylviologen benzylviologen, and Wurster's blue.

The next group of compounds are heterocyclics having one nitrogen and a second heteroannular member which is chalcogen (oxygen or sulfur). These compounds will for the most part have the following formula.

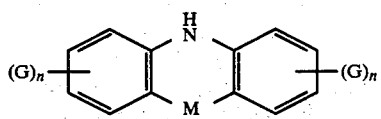

wherein
M is chalcogen (oxygen or sulfur), G is alkyl, oxy, which includes hydroxy or alkoxy, or amino, which includes alkylamino and dialkylamino, wherein the alkyl groups are of from 1 to 6, usually of from 1 to 3 carbon atoms, or adjacent Gs may be taken together to form a fused benzene ring with the annular carbon atoms to which they are attached; and n is of from 0 to 2, usually of from 1 to 2.

The total number of heteroatoms will normally be of from 2 to 6, more usually of from 4 to 6, and the total number of carbon atoms will normally be of from 12 to 20, more usually of from 12 to 16. Illustrative compounds include brillant cresyl blue, methylene blue and Meldola Blue.

In each instance, the compound will be functionalized to provide for a linking group for binding to the ligand. As indicated previously, the linking group for bonding ligand analog to the hub nucleus can also be employed for linking the label to the ligand. In effect, a hydrogen atom of the label will be substituted with a functionality which provides for covalent bonding to the ligand.

A wide variety of complex metal compounds can be employed as the label. Illustrative of metals are cobalt and iron, which may be complexed with porphyrins, phthalocyanines, phenanthrolines or other convenient complexing agents.

The electron transfer agents may be varied widely and will depend upon the label employed as well as the correlative electron transfer agent. Included among electron transfer agents are dihydropyridines illustrated by 1-benzyl-1,4-dihydronicotinamide, NADH, and Hanztsch ester (having alkyl esters of from 1 to 6 carbon atoms), thiols, ascorbic acid, reductone, phenylhydrazine, hydrazine, Nile Blue A, Safranine T, Phensafranine, Janus Green and viologens. These compounds will normally be employed as electron sources, providing for two electron transfers.

A wide variety of compounds can be employed as electron recipients, normally receiving one electron. These compounds include oxygen, methemoglobin, metmyoglobin, pentacyanonitrosoferrate, naphthoquinones, nitroxides, nitramine, metal complexes, such as cobalt, iron, molybdenum and vanadium, metallocenes, particularly of titanium and vanadium, methylene blue, viologens and tetrazolium salts.

The following table provides various pairs of electron transfer reagents and an appropriate label. For each of the references, the various reactants and catalysts which were tested are reported. Frequently, a number of different combinations were employed.

TABLE I

| Reference | Electron Transfer Agent, $R^2$ | Label | Electron Transfer Agent, $R^1$ |
|---|---|---|---|
| 1 | NADH derivatives | FMN | $O_2$ |
| 2 | NADH | FMN | Methmoglobin |
|  |  | FAD | Metmyoglobin |
|  |  | Methylene Blue |  |
| 3 | NADH | FMN | Na$_2$FeCN$_5$NO |
| 4,5,6 | N-benzyl 1, 2-dihydronicotinamide (I) | Riboflavin | $O_2$ |
|  |  | Neutral Red | 2,2,6,6-tetramethyl-piperidone-4-oxyl-1 |
|  | 2,6-dimethyl-3,5-dicarboethoxy-1,4-dihydropyridine (II) | FMN Galactoflavin |  |
|  | bis-2,2'-di(N-benzyl dihydronicotinamide) | Methylene blue 4,6-di-(tert-butyl)-o-benzoquinone | p-NOdimethylaniline nitramine |
|  |  |  | CO$^{+3}$, FE$^{+3}$, Mo and |
|  |  | 1,2-naphthoquinone alizarin dibromophenol indophenol | Va acetylacetonate Biscyclopentadienyltitanium dichloride |
|  |  | dichlorophenol indophenol | Biscyclopentadienylvanadium dichloride |
| 4 | Na$_2$S$_2$O$_4$ | N-propyl 1,4-dihydro- | 2,4,6-tri(tert-buty |

TABLE I-continued

| Reference | Electron Transfer Agent, $R^2$ | Label | Electron Transfer Agent, $R^1$ |
|---|---|---|---|
| | | nicotinamide | phenoxyl radical |
| 7 | Thiol (mercaptoethanol) | Vitamin $B_{12}$ | Methylene Blue |
| | NaSH | iron porphyrin | Nile Blue A |
| | ascorbic acid | Factor B | Safranine T |
| | reductone | Cyanocobalamin | Janus green |
| | phenylhydrazine | Hemin | benzyl viologen |
| | hydrazine | meso-tetra(p-carboxyphenyl)-porphino cobalt | methyl viologen |
| | | Co phthalocyanine | |
| 8 | II | phenazinemethosulfate | methyl viologen |
| | | pyocyanine | triphenyltetrazolium |
| | | | anthraquinone |
| | | | acenaphthenequinone |
| 9 | I | Wurster's Blue | $O_2$ |
| 10 | I | 2,6-diiodo-4-aminophenol | $O_2$ |
| | pyronine(H) | Meldola Blue | iron complex |
| | NADH | Meldola Blue | triphenyltetrazolium |

1. Wu et al, Biochemistry 9, 2219 (1970)
2. Brown & Synder, J. Biol. Chem. 244, 6702 (1969)
3. Fox & Tollin, Biochemistry 5, 3873 (1960)
4. Mozzhukin et al, Zhur. Obsh. Khim. 37, 1494 (1967)
5. Aleksandrova et al, Dokl. Akad. Nauk. SSR 167, 1291 (1966)
6. Zelenin et al, Zhur. Obsh. Khim. 37, 1500 (1967)
7. Schrauzer & Sibent, Arch. Biochem. Biophys. 130, 257 (1969)
8. Kito et al, Chemistry Letters 1974, 353
9. Bechara & Cilento, Biochemistry 11, 2606 (1972)
10. Cilento & Arauyo, Chem. Comm. 1968, 1420

For the most part, the electron transfer reagents will be small molecules, generally of molecular weight in the range of about 34 to 1,000, usually in the range of about 100 to 800. In order to enhance the steric inhibition by the receptor of the approach of one or both of the redox reactants, one or both of the redox reactants may be covalently or non-covalently bound to a macromolecular water soluble molecule.

When the redox reactant is covalently bound, the same linking groups and same hub nucleii may be employed as were employed for linking the ligand analog and label to the hub nucleus. Where non-covalent binding occurs, for example, a lipophilic substance to serum proteins, no covalent binding is required, although covalent binding may be desirable.

Antilabel

The antilabel is a receptor for the label, which binds to the label specifically, is inhibited from approaching the label by the presence of antiligand adjacent to the label, and inhibits the approach of the redox reactants to the label. Most conveniently, the antilabel will be an antibody prepared in conventional ways. The serum containing the antilabel may be purified e.g. affinity chromatography or used unpurified.

In choosing a particular system, a number of considerations will be involved. A first consideration is the ease with which the label may be conjugated to the ligand. A second consideration is the effect of the assay medium and the materials in the assay medium on the label. A third consideration is the rate of the catalyzed reaction, both in an absolute sense and in comparison to the uncatalyzed reaction. A high rate is desirable for the catalyzed reaction and a low rate for the uncatalyzed reaction. A fourth consideration is the ease with which the approach of the electron transfer reagent may be inhibited by the presence of antiligand on the labeled ligand. Included in this consideration is the size of the electron transfer reagents or the ease with which a small electron transfer reagent may be conjugated to a hub nucleus. A fifth consideration is the ease with which a product of one of the electron transfer reagents may be detected. This will depend upon the nature of the signal provided by the product, the size of the signal, as well as the sensitivity of available equipment. A sixth consideration is the ease with which interfering materials may be removed. For example, if oxygen affects the system, it may be necessary to carry out the assay in an inert medium or allow for the effect of the oxygen on the result. If the redox reactants are small and conjugation is undesirable, then antilabel may be used as an alternative.

The types of compounds which find use as the two electron transfer reagents are preferably dihydropyridines, which include the N-substituted dihydropyridines, Hanztsch ester, NAD, NADP, dihydronicotinamide, and the like. Preferred labels are those derivatives of acridine having the 9 carbon atom substituted with chalcogen (oxygen or sulfur) or nitrogen, namely phenazine, phenoxazine and phenothiazine.

Preferred single electron transfer agents include coordinate covalent metal complexes, such as ferric bisphenanthroline dioxo complexes, stable free radicals, and dyes, such as triphenyltetrazolium salts and methylene blue.

An illustrative method for linking a dihydropyridine to a hub nucleus to enhance molecular weight may be found in Larsson and Mosbach, FEBS Letters 46 119 (1974).

Kits

In carrying out the subject assays, in order to obtain reproducible results, it is necessary that the critical reagents be provided in predetermined ratios, so as to optimize the sensitivity of the assay. In the assay for ligand, the critical reagents are labeled ligand (includes poly(ligand analog)-polylabel), antiligand, and optionally antilabel. Since the electron transfer reagents will be present in relatively large amounts, small variations in their concentrations will tend to have only minor effects on the results. Besides the necessity to have the critical reagents in predetermined proportions, it is frequently desirable that ancillary materials, such as buffer, stabilizers, and the like, be included with the critical reagents, so that dry powders or concentrates may be diluted to form assay solutions directly, avoiding the necessity of weighing the various materials. Furthermore, where Fab fragments are employed, the labeled ligand and Fab fragment may be joined as a single reagent.

In a kit, the labeled ligand and antiligand will be provided in relative proportions, so as to substantially optimize the sensitivity of the assay through the concentration range of interest. In addition, included with one or both of the reagents may be buffer, inert proteins, such as albumins, stabilizers, such as sodium azide, and the like.

The following examples are offered by way of illustration and not by way of limitation.

EXPERIMENTAL (All temperatures not otherwise indicated are in centigrade. All percents or parts not otherwise indicated are by weight except for mixtures of liquids which are by volume.)

Ex. I Meldola Blue Conjugate to human gamma-globulin (hIgG)

A. N-Methyl-N(3-carboxypropyl)-aniline

Ethyl 4-bromobutyrate (20.4 g, 0.105 mole) and N-methyl aniline (10.8 g, 0.101 mole) were heated together at 105° for 18 hr. The reaction mixture was poured into saturated aqueous sodium bicarbonate and extracted with benzene (30 ml). The organic layer was evaporated to give a viscous oil.

The oily ester was heated at 110° for 4 hrs with a solution of 6 g sodium hydroxide in 40 ml water. The resulting solution was washed with 2×25 ml benzene, then acidified to pH 6 with concentrated hydrochloric acid (12 ml). The precipitated oil was extracted with 2×25 ml chloroform. The extracts were dried and evaporated, and the residue distilled to give the anilino acid.

B. p-Nitroso-N-methyl-N-(3-carboxypropyl)-aniline hydrochloride

The anilino acid prepared above (12.7 g, 66 mmole) was dissolved in 6N hydrochloric acid (45 ml) and cooled to 5° in an ice bath. Sodium nitrite (5.5 g, 80 mmole) in water (10 ml) was added slowly over 30 min. The mixture was stirred an additional 1 hr at 5°. The precipitated nitroso compound was filtered off, washed with 6N hydrochloric acid (25 ml), ethanol (10 ml), and air dried to give the nitroso hydrochloride as a yellow powder (13.4 g, 52 mmole, 79% yield).

C. Carboxypropyl Meldola Blue

The nitroso hydrochloride prepared above (13.4 g, 52 mmole) and 2-naphthol (7.5 g, 52 mmole) were dissolved in ethanol (50 ml) and water (25 ml) and heated at reflux for 1 hr. The deep blue solution was diluted with water (1 l.), stirred ½ hr, decanted from the tars and filtered. The tars were taken up in ethanol (100 ml), diluted with water (1 l.), and filtered. The combined filtrates were stirred for 12 hrs while air was bubbled through the solution. The resulting mixture was filtered. The filtrate was treated with 70% perchloric acid (10 ml) and stirred overnight. The precipitated perchlorate salt of the dye was collected and recrystallized from ethanol (200 ml) to give carboxypropyl Meldola Blue perchlorate as a dark powder (4.4 g, 10 mmole, 20% yield).

D. NHS Ester of Carboxypropyl Meldola Blue

Carboxypropyl Meldola Blue (47 mg, 0.1 mmole), N-hydroxysuccinimide (12 mg, 0.1 mmole), and 1-ethyl-3-dimethylaminopropylcarbodiimide hydrochloride (22 mg, 0.11 mole) were dissolved in dry dimethylformamide (1.0 ml) and stirred at room temperature for 1 hr, then stored at 5° for 18 hr. The resulting solution was used for the subsequent conjugation to hIgG.

E. Meldola Blue — hIgG Conjugate hIgG (5 mg) and NADH (5 mg) were dissolved in a dimethylformamide-water buffer (0.5 ml) (prepared from 0.35 ml 50 mM $K_2HPO_4$ and 0.15 ml dimethylformamide). A solution of the NHS ester of carboxypropyl Meldola Blue in dimethylformamide (5 $\mu$l of the solution described above) was added. The brownish solution was stored at room temperature for 3 hrs, then chromatographed on Sephadex G-50, using a saline phosphate buffer, pH7, as eluant. The purple protein fraction was collected, stored overnight, and re-chromatographed to give a solution of the Meldola Blue-hIgG conjugate with $A_{560}$ = 0.21 and $A_{278}$ = 0.86, corresponding roughly to an hIgG concentration of $3 \times 10^{-6}M$, and a conjugate number of 2-3.

Ex. II Preparation of Meldola Blue — Morphine Conjugate

To a solution of O-(2-aminoethyl)morphine (4 mg) in dichloromethane (1 ml) was added carboxypropyl Meldola Blue perchlorate (6 mg) and N-ethyl,N'-dimethylaminopropyl carbodiimide hydrochloride (6 mg). After the reaction was complete (as judged by TLC of the reaction mixture), 100 $\mu$l of the resulting solution was separated by TLC on silica gel (20% MeOH/CHCl$_3$). The conjugate was recovered from the appropriate band by elution with methanol containing concentrated hydrochloric acid (one drop/ml). The resulting solution was evaporated. The residue was dissolved in methanol (1 ml) and filtered. The filtrate was again evaporated. The residue was then dissolved in methanol (three drops), diluted with phosphate buffer (20 mM, pH7, containing 0.15M NaCl; 1 ml) and again filtered. The resulting stock solution of the Meldola Blue — Morphine conjugate was analyzed by spectroscopy for Meldola Blue and by a homogeneous enzyme immunoassay (EMIT ®) supplied by Syva Co.) for morphine. The analysis showed the solution to be $3 \times 10^{-5}M$ in Meldola Blue and $3-5 \times 10^{-5}M$ in morphine, in keeping with the presence of a 1:1 conjugate of Meldola Blue and morphine.

In order to demonstrate the subject invention, the following assays were carried out. The following reagents were employed in the first assay.

Buffer — 22 ml 0.02M phosphate buffer, pH7, with 0.15M NaCl.

2.5 ml dimethylformamide 25 mg triphenyltetrazolium salt (INT) (Nutritional Biochemicals)

250 mg Rabbit serum albumin (Sigma)

NADH — 200 mg NADH (Calbiochem) in 1.0 ml deionized water.

Antibody — 300 $\mu$l anti-hIgG, 2.4 mg/ml (Miles Laboratories)

200 $\mu$l deionized water

Conjugate — 200 μl Meldola Blue-hIgG (as described above)

300 μl deionized water hIgG — Stock solution of 3.0 mg hIgG (Miles Laboratories) and 1.0 ml deionized water diluted (a) 1:201
(b) 1:101
(c) 2:102
(d) 4:104
(e) 6:106
(f) 10:110
(g) 10:60

The following protocol was employed. Into 500μl of buffer was dissolved 25μl of the antibody solution and 25μl of the hIgG solution and the mixture incubated at room temperaure for 10 min. This was followed by the addition of 25μl of the Meldola Blue-hIgG conjugate solution in 250μl of buffer and the solution mixed and incubated for 20 min. At the end of this time, 25μl of the NADH solution in 250μl of buffer were added and the rate of INT reduction measured by the increase in absorbance at 492 nm over a 3 min. period using a Gilford 300-Microsample Spectrophotometer. The molar concentrations of the various materials in the assay medium were as follows: NADH $8.5 \times 10^{-3}$; INT $2.4 \times 10^{-3}$; Meldola Blue-hIgG conjugate $3 \times 10^{-8}$; anti(hIgG) $2.4 \times 10^{-7}$; and hIgG $0-8 \times 10^{-8}$. The following table indicates the results.

| Concentration of hIgG in assay mixture | Rate* ($\Delta A_{492}$ in 3min.) |
| --- | --- |
| 0 | 0.084 |
| $2.4 \times 10^{-9}$ | 0.084 |
| $4.8 \times 10^{-9}$ | 0.085 |
| $9.2 \times 10^{-9}$ | 0.090 |
| $1.8 \times 10^{-8}$ | 0.097 |
| $2.7 \times 10^{-8}$ | 0.106 |
| $4.3 \times 10^{-8}$ | 0.115 |
| $8.0 \times 10^{-8}$ | 0.117 |
| Rate in absence of either $IgG_H$ or anti-$IgG_H$ | 0.109 |

*temperature - 30°

The next assay employed the morphine - Meldola Blue conjugate of Example II. The following reagents were employed. II. Demonstration of Assay for Morphine A. Reagents 1. Buffer — 500mg rabbit serum albumin (Sigma) 50mg triphenyltetrazolium salt (INT) dissolved in 1ml DMF
Conc. in assay 1.6mM
Both dissolved in
50ml PBS (0.02M phosphate buffer, pH7, with 0.15M NaCl).

2. NADH — 250mg NADH (Calbiochem) + 2.50ml PBS conc. in assay 5mM.

3. Anti-morphine — 20μl Morphine antiserum, + 3.00ml PBS.

4. Meldola Blue — Morphine Conjugate — 40μl of stock solution described above + 200ml PBS. Conc. in assay, $2.5 \times 10^{-8}$M.

B. Morphine Solutions

1. Stock — 106mg morphine in 100ml methanol.
2. Morphine sample solutions

| | Conc. in Sample | Conc. in Assay |
| --- | --- | --- |
| a) M1000 - 50μl stock + 10000μl PSB | 175μM | 7.3μM |
| b) M100 - 100μl M1000 + 1000μl PBS | 16μM | 0.66μM |
| c) M30 - 100μl M100 + 200μl PBS | 5.3μM | 0.22μM |
| d) M10 - 100μl M100 + 1000μl PBS | 1.45μM | 0.06μM |
| e) M3 - 30μl M100 + 1000μl PBS | 0.47μM | 0.019μM |
| f) M1 - 10μl M100 + 1000μl PBS | 0.16μM | 0.007μM |
| g) M0 - 0μl M100 + 1000 μl PBS | 0μM | 0μM |

The following protocol was employed. The conjugate solution (50μl) in 250μl buffer and 50μl of morphine sample solution in 250μl buffer were mixed. Antimorphine solution (50μl) in 250μl buffer was added and the solution mixed. NADH solution (50μl) in 250μl buffer was added, the solution mixed, and the rate of INT reduction at 30° was measured by the increase in absorbance at 492nm over a 3min. period using a Gilford 300-microsample spectrophotometer. Measurement for each morphine sample was related to the rate with no morphine present (MO) and with a saturating level of morphine (M1000).

The following table indicates the results.

| Sample | Rate for MO | Rate for Sample | Rate for M1000 | $\frac{\text{Sample} - \text{MO}}{\text{M1000} - \text{MO}} \times 100$ |
| --- | --- | --- | --- | --- |
| M1 | 117 | 117 | 153 | 0 |
| M1 | 106 | 110 | 148 | 10 |
| M3 | 113 | 115 | 153 | 4 |
| M3 | 106 | 109 | 143 | 8 |
| M10 | 113 | 122 | 148 | 26 |
| M10 | 102 | 114 | 143 | 29 |
| M30 | 110 | 132 | 148 | 58 |
| M30 | 102 | 124 | 134 | 69 |
| M100 | 110 | 137 | 148 | 71 |
| M100 | (98)* | 125 | 134 | 71 |

*extrapolated value

The results are summarized as follows.

| Conc. of Morphine | | Rate as % Response in Assay |
| --- | --- | --- |
| Sample | Assay | |
| 0.16μM | 0.007μM | 5 ± 5 |
| 0.47 | 0.019 | 6 ± 2 |
| 1.45 | 0.06 | 27 ± 2 |
| 5.3 | 0.22 | 63 ± 6 |
| 16 | 0.66 | 71 |

Lower limit of detection then is ca. 50nM in assay, or ca 1 μM in sample.

It is evident from the above results that a sensitive assay technique is provided for the determination of both haptens and antigens. Simple stable chemicals are employed. Conveniently, with NADH and INT, there is no need for covalent bonding of a redox reactant to a large hub nucleus. The period of determination is short and the protocol simple involving few manipulative steps.

A novel assay method has been provided which employs stable reagents and allows for a variety of methods of detecting the rate of change as effected by available receptor for binding to a labeled ligand. A wide variety of labels can be used, which allows for substantial flexibility in electron transfer reagents. Thus, different systems can be employed, depending on the needed sensitivity, the nature of the ligand involved and materials found in the medium to be assayed. The method is fast, can employ readily available equipment, and employs reagents which can be stored for long periods of time without deterioration or change in their activity.

Although the foregoing invention has been described in some detail by way of illustration and example for purposes of clarity of understanding, it will be obvious that certain changes and modifications may be practiced within the scope of the appended claims.

What is claimed is:

1. A method for measuring an analyte suspected of being present in an unknown, wherein said analyte is a member of an immunological pair consisting of ligand and antiligand, wherein three reactants are employed;
   (1) conjugated label, wherein said label is conjugated either directly or indirectly to ligand analog to form labeled ligand, wherein ligand analog is capable of competing with ligand for antiligand and said label is capable of reacting by both one and two electron transfers;
   (2) a redox reactant, $R^1$, which reacts by one electron transfer and is capable of reacting with said label; and
   (3) a redox reactant, $R^2$, which reacts by two electron transfer and is capable of reacting with said label, wherein the rate of the label mediated reaction between $R^1$ and $R^2$ is substantially greater than the rate of the direct reaction between $R^1$ and $R^2$ and wherein either one or the product of one of $R^1$ and $R^2$ provides a detectible signal;
   said method comprising;
      (a) combining in an aqueous assay solution:
         (i) said unknown;
         (ii) conjugated label;
         (iii) $R^1$;
         (iv) $R^2$; and
         (v) antiligand when said analyte is ligand; and
      (b) determining the rate of reaction between $R^1$ and $R^2$ as compared to said rate in an assay solution having a known amount of analyte.

2. A method according to claim 1, wherein said assay solution is buffered to a pH in the range of about 5 to 10 and is at a temperature in the range of about 10° to 50° C.

3. A method according to claim 2, wherein said pH is in the range of 7 to 9 and said temperature is in the range of about 15° to 40° C.

4. A method according to claim 2, wherein said analyte is a monoepitopic ligand.

5. A method according to claim 2, wherein said analyte is a polyepitopic ligand.

6. A method according to claim 6, wherein said analyte is an antiligand.

7. A method according to claim 2, wherein $R^2$ is a hydride transfer agent.

8. A method according to claim 2, wherein said hydride transfer agent is a dihydropyridine.

9. A method according to claim 2, wherein antilabel is included in said aqueous assay solution.

10. A method according to claim 2, wherein said label is capable of forming a quinone structure.

11. A method for measuring a ligand analyte suspected of being present in an unknown, wherein three reactants are employed;
    (1) conjugated label, wherein said label is capable of forming a quinone structure and is conjugated either directly or indirectly to ligand analog to form labeled ligand, wherein said ligand analog is capable of competing with said ligand for antiligand and wherein said label is capable of reacting by both one and two electron transfers;
    (2) a redox reactant, $R^1$, which reacts by one electron transfers and is capable of reacting with said label; and
    (3) a redox reactant, $R^2$, which reacts by two electron transfers involving the transfer of a hydride and is capable of reacting with said label;
    wherein the rate of the label mediated reaction between $R^1$ and $R^2$ is substantially greater than the rate of the direct reaction between $R^1$ and $R^2$ and wherein either one or the product of one of $R^1$ and $R^2$ provides a detectible signal;
    said method comprising;
       (a) combining in an aqueous assay solution;
          (i) said unknown;
          (ii) conjugated label;
          (iii) $R^1$;
          (iv) $R^2$; and
          (v) antiligand; and
       (b) determining the rate of reaction between $R^1$ and $R^2$ as compared to the rate in an assay solution having a known amount of ligand.

12. A method according to claim 11, wherein at least one of $R^1$ and $R^2$ is added to said assay solution after the combining of said unknown, conjugated label and antiligand.

13. A method according to claim 12, wherein said unknown is incubated with said antiligand.

14. A method according to claim 13, wherein said unknown and said antiligand are combined and incubated, followed by the addition of conjugated label, followed by a second incubation, wherein at least one of $R^1$ and $R^2$ is added after said second incubation.

15. A method according to claim 11, wherein $R^2$ is a dihydropyridine.

16. A method according to claim 15, wherein said dihydropyridine is NADH or NADPH.

17. A method according to claim 15, wherein said dihydropyridine is 2,6-dimethyl-3,5-dicarboalkoxy-1,4-dihydropyridine wherein the alkoxy group is of from 1 to 6 carbon atoms.

18. A method according to claim 11, wherein $R^1$ is a tetrazolium salt.

19. A method according to claim 11, wherein $R^1$ is a metal complex.

20. A method for measuring a ligand analyte suspected of being present in an unknown, wherein three reactants are employed;
    (1) conjugated label, wherein said label is capable of forming a quinone structure and is conjugated to a polyepitopic ligand to form labeled ligand, wherein said label is capable of reacting by both one and two electron transfers;
    (2) a redox reactant $R^1$ which reacts by a one electron transfer and is capable of reacting with said label; and
    (3) a dihydropyridine redox reactant $R^2$ which reacts by two electron transfer involving the transfer of a hydride and is capable of reacting with said label;
    wherein the rate of the label mediated reaction between $R^1$ and $R^2$ is substantially greater than the rate of the direct reaction between $R^1$ and $R^2$ and wherein either one or the product of one of $R^1$ and $R^2$ provides a detectible signal;
    said method comprising:

(a) combining in an aqueous assay solution at a pH in the range of 5 to 10 and at a temperature in the range of about 10° to 50° C.;
(i) said unknown;
(ii) conjugated label;
(iii) $R^1$;
(iv) $R^2$; and
(v) antiligand; and
(b) determining the rate of reaction between $R^1$ and $R^2$ as compared to the rate in an assay solution having a known amount of ligand.

21. A method according to claim 20, wherein $R^2$ is NADH, $R^1$ is a tetrazolium salt and said label is meldola blue.

22. A method according to claim 21, wherein said ligand is a polyamino acid.

23. A method according to claim 22, wherein said polyamino acid is a γ-globulin.

24. A method for measuring a ligand analyte suspected of being present in an unknown, wherein three reactants are employed;
(1) conjugated label, wherein said label is capable of forming a quinone structure and is conjugated to a monoepitopic ligand to form labeled ligand, wherein said label is capable of reacting by both one and two electron transfers;
(2) a redox reactant $R^1$ which reacts by a one electron transfer and is capable of reacting with said label; and
(3) a dihydropyridine redox reactant $R^2$ which reacts by two electron transfer involving the transfer of a hydride and is capable of reacting with said label; wherein the rate of the label mediated reaction between $R^1$ and $R^2$ is substantially greater than the rate of the direct reaction between $R^1$ and $R^2$ and wherein either one or the product of one of $R^1$ and $R^2$ provides a detectible signal;
said method comprising:
(a) combining in an aqueous assay solution at a pH in the range of 5 to 10 and at a temperature in the range of about 10° to 50° C.;
(i) said unknown;
(ii) conjugated label;
(iii) $R^1$;
(iv) $R^2$; and
(v) antiligand; and
(b) determining the rate of reaction between $R^1$ and $R^2$ as compared to the rate in an assay solution having a known amount of ligand.

25. A method according to claim 24, wherein $R^2$ is NADH, $R^1$ is a tetrazolium salt and said label is meldola blue.

26. A method according to claim 25, wherein said ligand is a drug of from about 125 to 1000 molecular weight.

27. A method according to claim 26, wherein said ligand is morphine.

* * * * *